(12) United States Patent
Novac

(10) Patent No.: US 7,988,638 B2
(45) Date of Patent: Aug. 2, 2011

(54) SIGNAL CONDITIONING CIRCUIT BETWEEN AN OPTICAL DEVICE AND A PROCESSING UNIT

(75) Inventor: Pinchas Novac, Neuchâtel (CH)

(73) Assignee: EM Microelectronic-Marin S.A., Marin (CH)

( * ) Notice: Subject to any disclaimer, the term of this patent is extended or adjusted under 35 U.S.C. 154(b) by 531 days.

(21) Appl. No.: 11/683,524

(22) Filed: Mar. 8, 2007

(65) Prior Publication Data

US 2007/0213020 A1 Sep. 13, 2007

(30) Foreign Application Priority Data

Mar. 8, 2006 (EP) .................................... 06110828

(51) Int. Cl.
*A61B 5/02* (2006.01)
(52) U.S. Cl. ........................ 600/500; 600/503
(58) Field of Classification Search .......... 600/500–503; 358/98; 250/214
See application file for complete search history.

(56) References Cited

U.S. PATENT DOCUMENTS

| | | | | |
|---|---|---|---|---|
| 4,333,475 A | * | 6/1982 | Moreno et al. ................. | 600/524 |
| 4,545,387 A | * | 10/1985 | Balique .......................... | 600/500 |
| 4,853,772 A | * | 8/1989 | Kikuchi ......................... | 348/71 |
| 5,795,300 A | * | 8/1998 | Bryars .......................... | 600/500 |
| 6,044,162 A | * | 3/2000 | Mead et al. .................... | 381/312 |
| 2003/0106989 A1 | * | 6/2003 | Bloehbaum et al. ...... | 250/214 A |
| 2006/0139093 A1 | * | 6/2006 | Gagon .......................... | 330/126 |

FOREIGN PATENT DOCUMENTS

| | | |
|---|---|---|
| DE | 103 18 764 A1 | 11/2003 |
| EP | 0 098 662 A1 | 1/1984 |
| EP | 0 262 779 A1 | 4/1988 |
| EP | 0 319 159 A1 | 6/1989 |
| EP | 1 484 009 A1 | 12/2004 |

OTHER PUBLICATIONS

"MOSFET," entry from Wikipedia online encyclopedia, page last modified Jul. 31, 2006, printed Aug. 23, 2006.
"Active Filler," entry from Wikipedia online encyclopedia, page last modified Jul. 18, 2006, printed Aug. 23, 2006.
European Search Report issued in corresponding application No. EP 06 11 0828, completed Aug. 23, 2006.

* cited by examiner

*Primary Examiner* — Patricia C Mallari
*Assistant Examiner* — Michael D'Angelo
(74) *Attorney, Agent, or Firm* — Griffin & Szipl, P.C.

(57) ABSTRACT

The invention concerns a conditioning circuit (10) for an external signal (IN) representative of a physiological quantity, arranged between an optical sensor (11) and a processing unit (12), the received external signal (IN) being broken down into a useful component and an ambient component, characterized in that the conditioning circuit includes a first stage (13) including a transimpedance amplifier with an incorporated high pass filter (15) using a feedback loop to subtract the ambient signal component from the received external signal, and to deliver at output an amplified useful signal (IN1), a second stage (16) including a blocker sampler circuit (17) for demodulating the amplified useful signal and delivering at output a demodulated useful signal (IN2), and a third stage (18) including a bandpass filter (19) for filtering the demodulated useful signal in the frequency band of the physiological quantity to be detected and for transmitting a conditioned signal (OUT) to the processing unit.

16 Claims, 10 Drawing Sheets

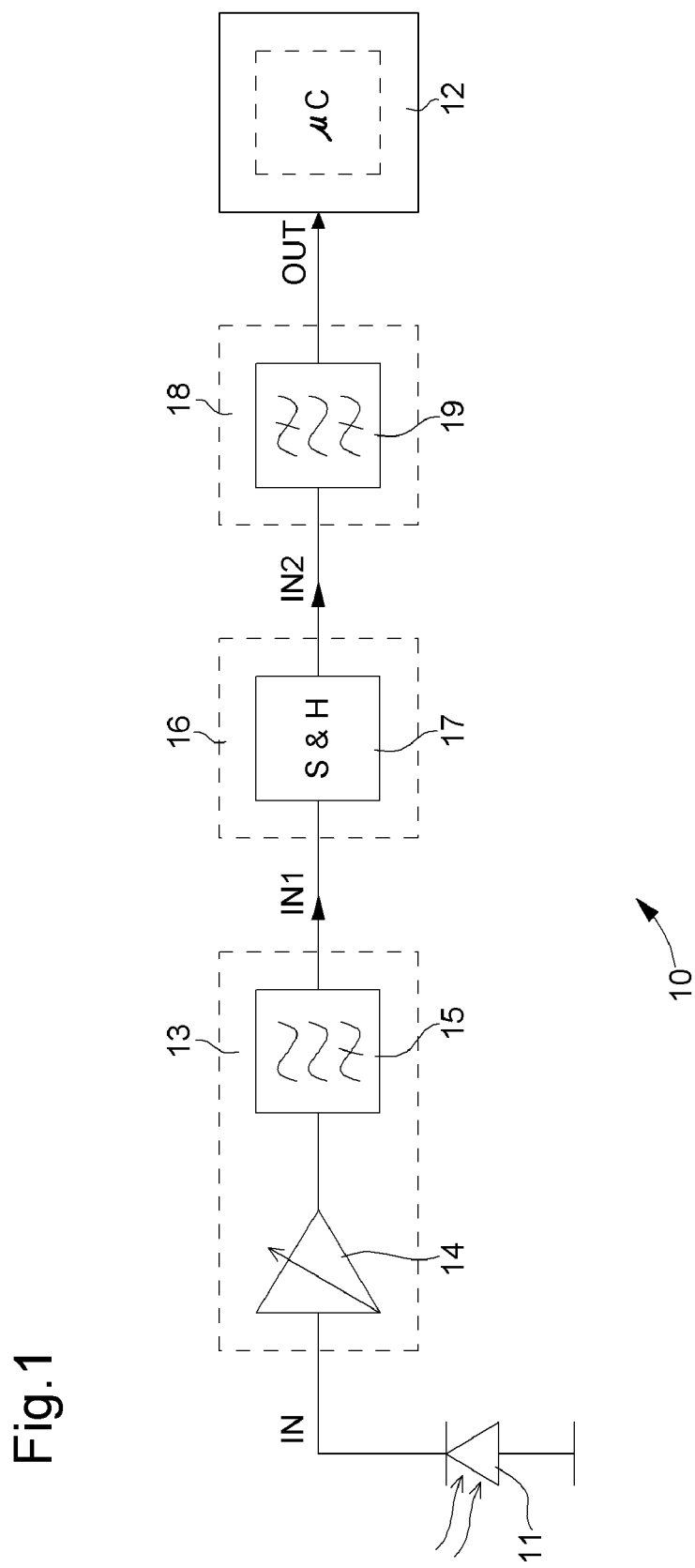

(Art antérieur)

SIGNAL CONDITIONING CIRCUIT BETWEEN AN OPTICAL DEVICE AND A PROCESSING UNIT

This application claims priority from European Patent Application No. 06110828, filed Mar. 8, 2006, the entire disclosure of which is incorporated herein by reference.

FIELD OF THE INVENTION

The present invention concerns, generally, a conditioning circuit for the signal between an optical sensor for measuring a physiological quantity, particularly the heart rate, and a digital processing unit for received signals. The invention concerns more specifically the various stages of the conditioning unit, in particular, the amplification, locking sampling and filtering stages. The invention also concerns an integrated circuit comprising this conditioning circuit. The invention further concerns a portable electronic instrument including such an integrated circuit.

BACKGROUND OF THE INVENTION

There is known from the prior art, in particular from EP Patent No. 1 484 009, a portable instrument provided with an optical device for measuring a physiological quantity. This document describes in particular, as shown in FIG. 6, a portable instrument including a light source 61 (for example a light emitting diode, i.e. LED, or any other suitable device) coupled to a control circuit 71, whose operation is controlled by a central processing unit 70, such as a microprocessor or microcontroller. This central unit 70 is further interfaced with a display device 73 (of analogue and/or digital type), storage means 74 (RAM, ROM, EEPROM FLASH or the like) and a clock system 75, for properly clocking the operation of central unit 70 and its peripheral components. This clock system 75 can further perform the conventional clock functions of a timekeeper.

The central processing unit is also coupled to a circuit 72 dedicated to detection of the desired physiological quantity measurement, for example the heart rate or the level of oxygen in the blood, the functions of this circuit being able to be integrated with those of central processing unit 70. This circuit extracts data relative to the physiological quantity from optical signals detected by the associated photoreceptor(s). In this case, a first photoreceptor 62 is coupled to detection circuit 72 by amplification and, if necessary, filtering means 63. Data relating to the desired physiological quantity is transmitted to central processing unit 70, particularly in order to be displayed on device 73 and/or stored in storage means 74 for subsequent consultation.

According to one embodiment that can be envisaged, shown in FIG. 7, an amplifier in series with a high pass filter is provided for making the amplification and filtering means at the output of the photoreceptor. The external signal IN is first of all amplified through an amplifier circuit 81, performing a current voltage converter function. In addition to amplifier circuit 81, the first stage comprises a high pass filter 82 that can be made for example by means of a Sallen Key type high pass filter with a finite gain amplifier. Thus, the ambient component of external signal IN, which is not modulated, is removed through the high pass filter 82. An amplified IN1 signal, comprising only the useful component of the detected signal, is transmitted at the output of the amplification and filtering means to the next stage for conditioning of the signals.

Nonetheless, within the scope of the present invention, it has been demonstrated that this solution is not optimal insofar as the ambient signal that is a component of the received external signal IN is also amplified through amplifier 81, which considerably limits the usable gain range of the amplifier to prevent the latter becoming saturated. The noise over signal ratio would then be less advantageous at the input of the following stage.

Moreover, this portable instrument and more particularly the conditioning circuit for conditioning the signals received by the optical sensor prior to processing by the central processing unit, has certain drawbacks, particularly in terms of the space occupied in the portable instrument and in terms of power consumption. Indeed, in this portable electronic instrument, two major concerns are typically the available space and power consumption which are both limited. A conditioning circuit like that presented in the prior art has a non-optimum occupied surface area in that it uses a certain number of discrete components to perform the functions of amplification, filtering and detection. Moreover, each of these functions has non-optimised energy consumption because of the use of numerous operational amplifiers.

SUMMARY OF THE INVENTION

One of the main objects of the present invention is to overcome the aforementioned drawbacks by implementing a conditioning circuit between an optical sensor and a processing unit at least part of whose elements have been integrated and whose energy consumption has been optimised.

The present invention therefore concerns a conditioning circuit for an external signal representative of a physiological quantity between an optical sensor and a processing unit, the received external signal being broken down into a useful component and an ambient component, characterized in that the conditioning circuit comprises a first stage including a transimpedance amplifier with an incorporated high pass filter using a feedback loop for subtracting, at the stage input, the ambient signal component from the received external signal and for delivering, at output, an amplified useful signal, a second stage comprising a locker sampling circuit for demodulating the amplified useful signal and delivering at output a demodulated useful signal, and a third stage comprising a bandpass filter for filtering the demodulated useful signal in the frequency band of the physiological quantity to be detected and for transmitting a conditioned signal to the processing unit.

Advantageous variants of this conditioning circuit are given in relation to the dependent claims.

The invention also concerns an integrated circuit comprising a conditioning circuit according to the invention.

Finally, the present invention also concerns an electronic instrument worn on the wrist comprising an optical device for measuring a physiological quantity, particularly the heart rate, the optical device comprising at least one light source for subjecting one portion of an organic tissue to a light emission and at least one optical sensor for detecting the intensity of the light emission after propagation in the organic tissue, an integrated circuit comprising a conditioning circuit according to the invention and arranged for processing the optical signals detected by the optical sensor, and a display device for displaying information relating to the physiological quantity measurement, particularly the heart rate.

BRIEF DESCRIPTION OF THE DRAWINGS

Other features and advantages of the present invention will appear more clearly upon reading the following detailed description of embodiments of the invention given solely by way of non-limiting example and illustrated by the annexed drawings, in which:

FIG. 1 is an operational block diagram showing the whole of the conditioning circuit according to one embodiment of the invention;

FIG. 2b shows a preferred implementation example of the embodiment of the first stage of FIG. 2a;

DETAILED DESCRIPTION OF THE INVENTION

The various embodiments that will now be presented are given solely by way of non-limiting illustration. FIG. 1 is a flow chart showing the whole of conditioning circuit 10 according to one embodiment of the invention. For the sake of general comprehension, FIG. 1 also shows an optical sensor 11, like for example a photodiode, a phototransistor or any other suitable optical receiver receiving an external signal IN for measuring a physiological quantity, particularly the heart rate. This external signal IN is a current signal comprising an ambient component and a useful component, said signal being obtained for example by means of an optical device including at least one light source (not shown) for subjecting a portion of an organic tissue to a light emission and at least one photoreceptor, i.e. optical sensor 11, for detecting the intensity of the light emission after propagation in the organic tissue. A central processing unit 12 is also shown, such as a microprocessor or microcontroller receiving at input, by means of an analogue digital converter, the conditioned external signal OUT through the conditioning circuit 10 for processing the received signals.

Figure 7:
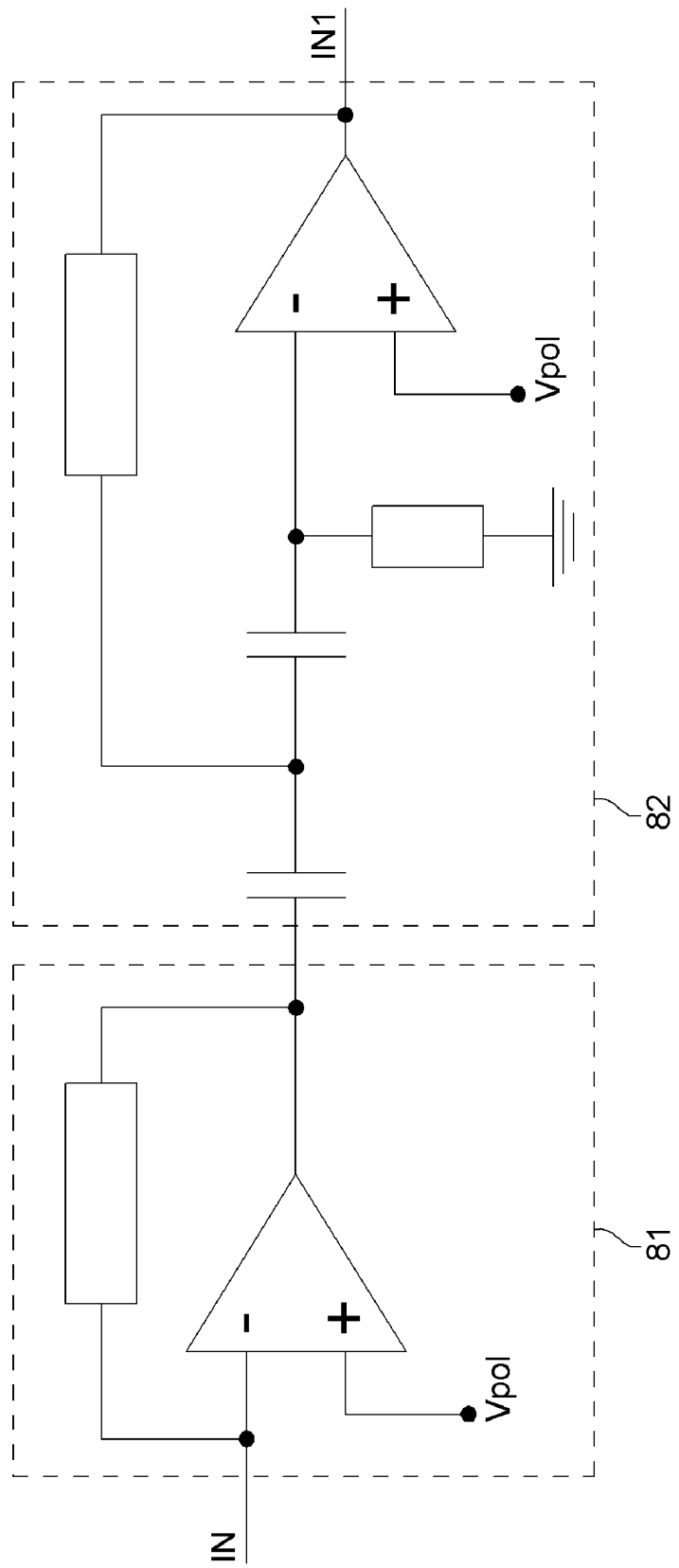
FIG. 7 is a flow chart of one embodiment of the first stage of the conditioning circuit.

Conditioning circuit 10 according to the invention performs this processing while optimising energy consumption compared to conventional solutions. This conditioning circuit comprises in particular a first transimpedance amplifier stage 13 for pre-amplifying the external signal IN and converting the current detected into a voltage. The signal is then filtered to remove the unmodulated low frequency components. Generally, in order to do this, the external signal IN is first of all amplified through an amplifier circuit 14, performing a current voltage converter function, then filtered by means of an high pass filter 15 that can be achieved for example by means of a Sallen Key type low pass filter with a finite gain amplifier. In order to overcome the drawbacks of a first stage like that shown in relation to FIG. 7, advantageous variants of the first stage 13, presented in more detail in relation to FIGS. 2a and 2b, comprise a feedback loop that only amplifies the useful component of the IN signal, i.e. amplitude of the detected pulses, after filtering the ambient component of the signal by subtraction via the feedback loop, i.e. received ambient light, keeping only the frequencies lower than the light source modulation frequency, which optimises the usable amplification gain without any risk of saturation and provides a more favourable signal noise ratio.

Conditioning circuit 10 then comprises a second stage 16 called the locker sampler stage for demodulating the signal IN1 received at the output of the first stage 13. The function of this locker sampler stage 16 is to make useful signal IN1 continuous before supplying it to the input of the next stage. According to an advantageous variant of this second locker sampler stage 16 which will be described in detail in relation to FIG. 3b, a locker sampler circuit 17, which comprises correlated double sampling means for demodulating the useful signal, is used. These correlated double sampling means have the advantage of getting rid of the offset and noise error in 1/f. According to another advantageous variant of this second sampler stage, locker 17, which will be described in detail in relation to FIG. 3c, a locker sampler circuit comprising correlated double sampling means associated with a single active transistor in place of a follower amplifier, is used, which reduces energy consumption compared to a solution according to the aforementioned first variant.

The conditioning circuit further includes a third at least $5^{th}$ order bandpass filtering stage 18 for filtering the signal IN2 transmitted at the output of the second stage 16 in the frequency band of the desired useful signal. According to a variant, a switched capacitance circuit is used to make a $5^{th}$ order Bessel bandpass filter for reactivity reasons. This $5^{th}$ order filter includes a $3^{rd}$ order band pass filter followed by a $2^{nd}$ order bandpass filter, the details of which will be given in relation respectively to FIGS. 4b and 4c. According to another advantageous variant that will be detailed in relation to FIG. 4d, the bandpass filter only uses a single active transistor instead of an inverter operational amplifier for each of the first four stages of the filter, which reduces energy consumption and gets rid of the 1/f noise. Thus in the $5^{th}$ order filter according to this other advantageous variant, only the last stage is made with an operational amplifier because of constraints as regards output resistance, compatibility with the analogue digital converter of the processing means and output signal voltage swing. Moreover, the reference voltage of this last stage is imposed by that of the analogue digital converter of the processing unit, i.e. the microcontroller, whereas, advantageously, the reference voltage of the preceding stages is only dependent on the active transistors used. It will also be noted that the gain of the switched capacitances can be adjusted by modifying the capacitance ratios.

Figure 2A:
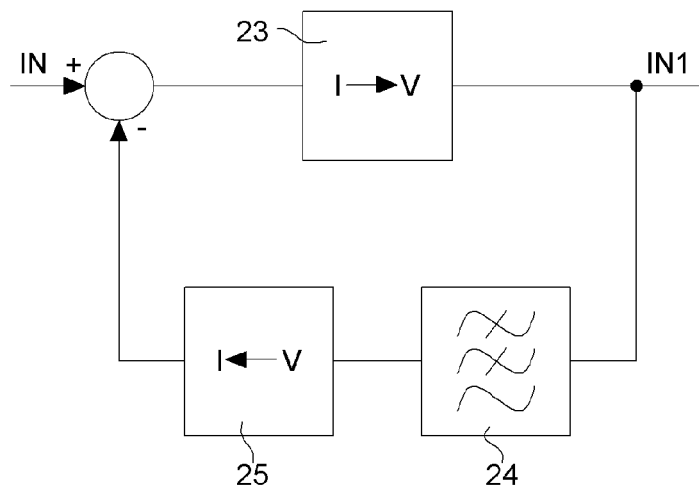
FIG. 2a is a flow chart of an advantageous embodiment of the first stage of the conditioning circuit according to the invention.

FIG. 2a is a flow diagram of the first stage of the conditioning circuit according to a preferred embodiment of the invention. The external signal IN is supplied to the input of a voltage current converter 23. A feedback loop is provided at the terminals of converter 23, comprising in series a low pass filter 24 and a current voltage converter 25. As was seen previously, the external signal IN includes an ambient component and a useful component corresponding to the useful signal that one wishes to detect and transmit to the processing unit. The purpose of the feedback loop is to separate the two components of the external signal IN. Thus, the function of the low pass filter 24 is to filter the high frequencies and particularly those carrying the useful signal component. Next, the purpose of the current voltage converter 25 is to reconvert the ambient component of the external signal in the form of a current to be subtracted from the received external signal IN. Thus, since the signal received at the input of the voltage current converter 23 is a signal that now only contains the useful component of the external signal IN, it is possible to use a voltage current converter with a much higher gain than that able to be used with a circuit shown in relation to FIG. 7 without any risk of saturation. By way of example, the received external signal IN is a current of the order of a microampere, whereas the useful component of this signal is of the order of a nanoampere, i.e. around a thousand times smaller. The feedback loop provided here thus allows the ambient component, which is of the order of a milliampere, to be subtracted and thus converter 23 receives only the useful component of the signal to be amplified, which is of the order of a nanoampere, enabling a higher gain to be used without increasing the risk of saturating converter 23 or the following stages that are also used as amplifiers. The useful signal IN1 is transmitted at the output of the first stage to be supplied to the input of the second stage.

Figure 2B:
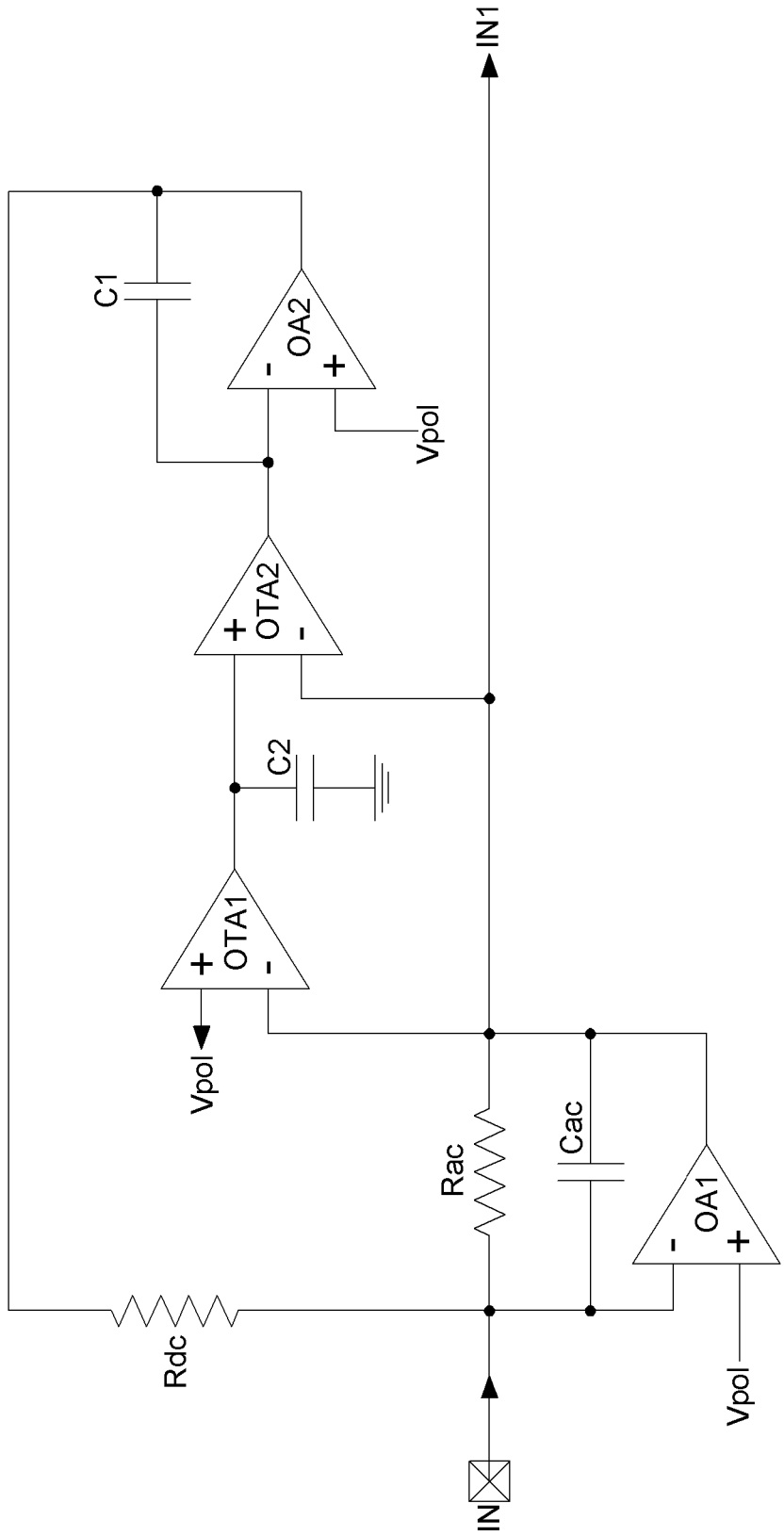

FIG. 2b is an advantageous variant of the embodiment of the first stage of the conditioning circuit of FIG. 2a. The voltage current conversion of voltage current converter 23 is performed by an operational amplifier OA1 and a inverse feedback resistor Rac. A capacitance Cac will preferably be connected in parallel to resistor Rac for reasons of stability.

In order to detect the continuous or ambient component of the received external signal IN, a inverse feedback circuit with two integrators is added, thus performing a $2^{nd}$ order transfer function, in accordance with the following formula:

$$\frac{V_{IN1}}{I_{IN}} = Rac \times \frac{s^2}{s^2 + (\omega_0/Q)s + \omega_0^2}$$

One way of implementing an equivalent transfer function consists of placing a low pass filter with an amplifier, also called a Sallen and Key filter, corresponding to a passive $2^{nd}$ order RC filter (not shown) and an operational filter. According to an advantageous implementation, all of the components of the $2^{nd}$ order low pass filter have been integrated. Thus, the resistors of the RC filter are integrated in the form of a transconductance operational amplifier (OTA1, OTA2).

According to another variant, it is possible to provide means for adjusting the gain of the operational amplifiers (OA1, OA2), for example by variable resistor Rac and capacitance Cac means for amplifier OA1, and a variable capacitance C1 for amplifier OA2. The gain adjustment can be programmed, particularly depending upon the user carrying a portable electronic instrument comprising the conditioning circuit. The adjustment criteria can be dependent for example upon the blood flow of the user and his level of effort. If the received external signals are powerful the gain could be decreased, conversely, if the received external signals are not powerful, the gain could be increased.

Resistance Rdc converts the voltage of the ambient component into a current that is subtracted directly at the input across which the external signal IN is received in the form of a current.

We will now consider in more detail variants of the second stage of the conditioning circuit shown in FIG. 1. The blocker sampling circuit operates like a demodulator, so that the circuit samples the signal IN1 transmitted at the output of the first stage during the second part of the sampling pulses and stores one sample between two pulses. Since it has a much greater time constant for following up the signal than for the sampling time, this circuit also integrates an anti spectrum aliasing filter, i.e. a low pass filter removing frequencies higher than the analogue signal to be digitalised to prevent spectrum folding. This self-integrated low pass filter also performs a noise removal function.

Figure 3A:
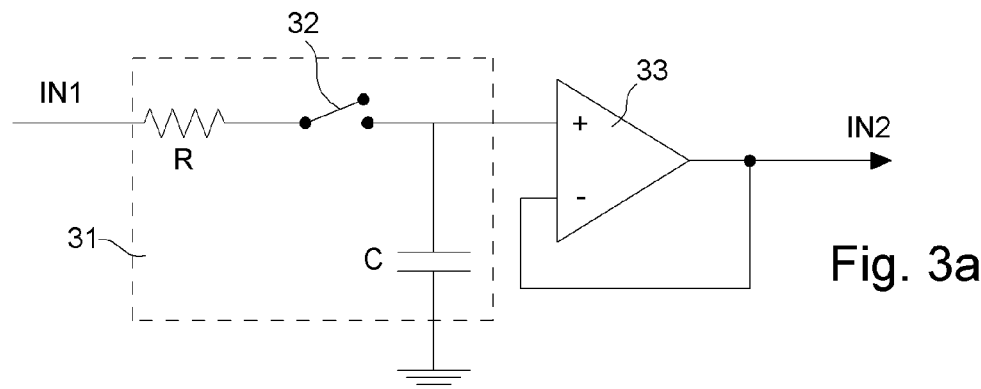
FIG. 3a is a flow chart according to one embodiment of the second stage of the conditioning circuit of the invention.

FIG. 3a shows an equivalent diagram of a blocker sampler circuit with an integrated filter able to be used in the conditioning circuit according to the invention. This circuit includes a low pass filter which is always active during the sampling phase. This low pass filter removes noise and operates like a spectrum anti aliasing filter. This can be achieved by using a time constant that is much greater than the sampling time. Thus, the circuit has a limited sweep speed. The filter frequency depends upon the ratio between the sampling time and the follow up time constant. For application to detection of the heart rate or blood oxygen level, one could for example envisage a filter frequency of 5 Hz. The equivalent circuit of this blocker sampler circuit includes an RC filter 31, a sampling switch 32 being provided between resistor R and capacitance C of filter 31. An operational amplifier 33 is provided at the output of filter 31 prior to transmission of the sampled and blocked signal IN2 to the third stage of the conditioning circuit.

Figure 3B:
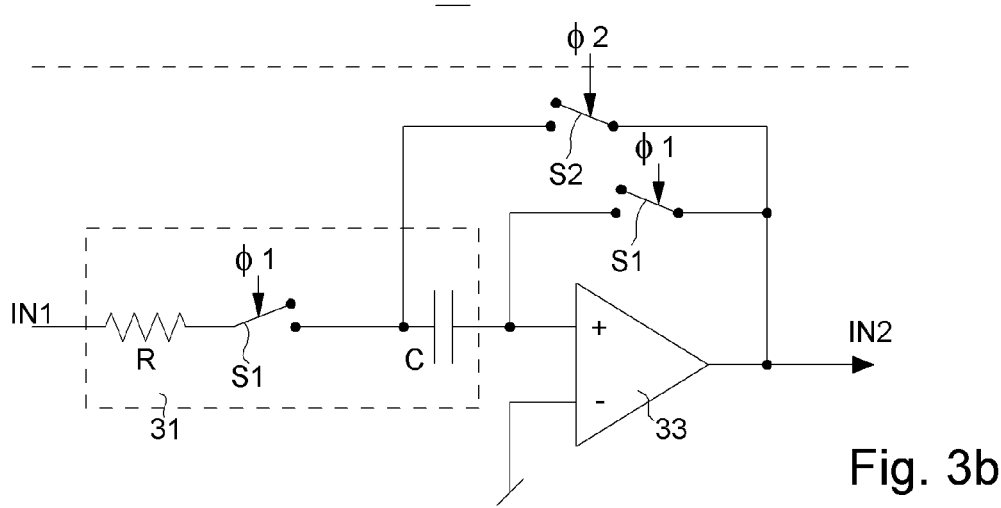
FIG. 3b is a flow chart according to another embodiment of the second stage of the conditioning circuit according to the invention.

FIG. 3b shows a correlated double sampling type blocker sampler circuit, which removes, in particular, offset error and 1/f noise. As in FIG. 3a, there is shown an RC filter 31 and an operational amplifier 33. However, sampling switch 32 has been replaced by three sampling switches (two S1, S2), whose control signals ($\phi_1$, $\phi_2$) are given in FIG. 3d. The first switch S1 is arranged between the resistor R and capacitance C of filter 31. Switch S2 is arranged between the first switch S1 and capacitance C, on the one hand, and the output of operational amplifier 33, on the other hand. Finally, the second switch S2 is arranged between the negative input and the output of operational amplifier 33.

Figure 3C:
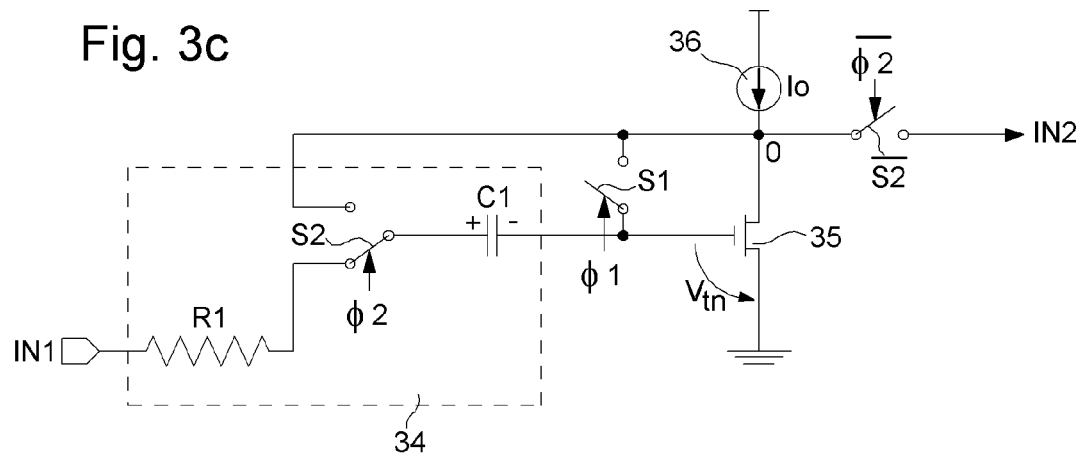
FIG. 3c shows a preferred implementation example of the second stage of the conditioning circuit.

FIG. 3c shows an example implementation of a correlated double sampling blocker sampler circuit using a single active transistor instead of operational amplifier 33 of FIG. 3b, which in addition to compensating for offset errors and 1/f noise, significantly reduces the current consumption of the second stage.

Figure 3D:
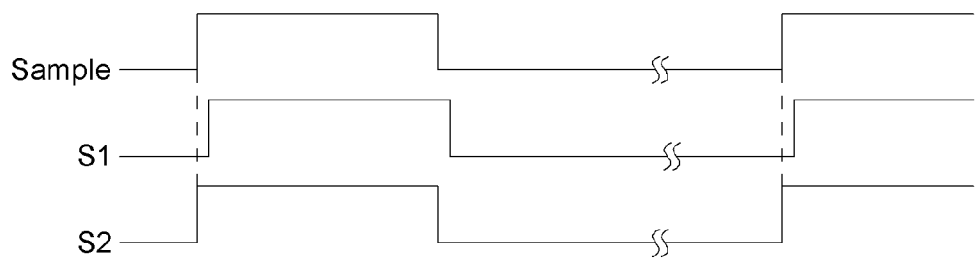
FIG. 3d shows the control signals applied at the second stage according to the embodiments of FIGS. 3b and 3c.

In this example embodiment of a correlated double sampling blocker sampler circuit, low pass filter 34 is formed by a R1C1 filter, three switches S1, S2 and $\overline{S2}$ whose activating phases ($\phi_1$, $\phi_2$) are shown in FIG. 3d, an active transistor 35 replacing the operational amplifier of the operational diagram of FIG. 3b, and a polarisation current source 36. The active transistor 35 is connected such that its gate, i.e. the control terminal, is controlled by the output of low pass filter 34, and its two current terminals are connected, one to the polarisation current source, and the other to a reference potential, for example the circuit earth. During the first phase, the sampling signal SAMPLE is for example at a high level, the control signals of switches S1 and S2 also both being at one level, it will be noted however, that the control signal S1 lags slightly relative to control signal S2, switch S1 thus being closed, i.e. conductive, slightly after switch S2 thus allowing time for capacitance C1 to be charged. During this first phase, S1 and S2 are thus closed, i.e. conductive, capacitance C1 is thus charged by the signal IN1 received at the input of the second stage transmitted at the output of the first stage less the threshold voltage of active transistor 35, namely $V_{C1}=V_{IN1}-V_{TN}$. Since switch $\overline{S2}$ is in the opposite state to switch S2, it is open during this first phase, i.e. not conductive, and the potential at the output of the second stage is disconnected from the third stage and is equal to the voltage of this active transistor threshold $V_0=V_{TN}$.

It will be noted in this example, shown in FIG. 3c, that active transistor 35 is an NMOS type transistor. It is however entirely possible to use a PMOS transistor instead, or even a bipolar technology transistor, by adapting the blocker sampler circuit in an appropriate manner.

During the second phase, the sampling signal is at a low level, as are the control signals of switches S1 and S2. Thus, the two switches S1 and S2 are then in the open position, i.e. non conductive, whereas switch $\overline{S2}$ is in the closed position, i.e. conductive. One of the terminals of capacitance C1 is floating, the other being connected to active transistor 35, the voltage at the terminals of capacitance C1 being the input voltage. In fact, the offset introduced by the threshold voltage of active transistor 35 is removed by this method of controlling switches S1 and S2. The output voltage $V_{IN2}$ is connected on the one hand to that of the second stage input, and on the other hand to the third stage input. The 1/f noise of active transistor 35 is compensated for, because of the low signal frequency.

Because useful signal IN2 is available at the output of the second stage during only one of the two phases ($\overline{\phi2}$), the filtering circuit of the third stage is clocked over the trailing edges of the clock signals.

The third stage of the conditioning circuit according to the invention comprises a bandpass circuit removing all of the frequencies that are not within the frequency band of the application. In the heart rate measurement example, the bandpass filter can thus be selected to keep only frequencies between 1 Hz and 5 Hz. This bandpass filter is advantageously made using the switched capacitance technique. Within the scope of the present invention, the necessity of using a filter of at least the $5^{th}$ order and preferably a $5^{th}$ order Bessel filter has been demonstrated, given that a $7^{th}$ order filter, while much more precise, is too slow and costly in terms of place and energy consumption.

Figure 4A:
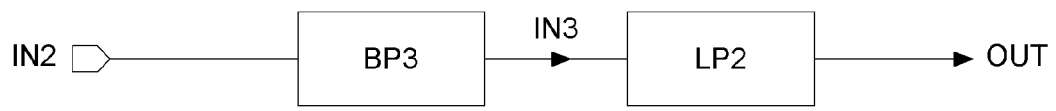
FIG. 4a is a flow chart according to one embodiment of the third stage of the conditioning circuit according to the invention.

As is shown schematically in FIG. 4a, the $5^{th}$ order bandpass filter is advantageously broken down into two sections, a first section comprising a $3^{rd}$ order bandpass filter BP3 and a second section comprising a $2^{nd}$ order low pass filter LP2. Because of the high continuous component of input signal IN2, the gain of this filter must be after the high pass stage of the $3^{rd}$ order bandpass filter.

The output impedance of the third stage must be adapted to the analogue digital converter of the processing unit receiving the conditioned signal OUT. This impedance adaptation depends in particular upon constraints imposed by the analogue digital converter. This is why, according to this definition, the output impedance of the source must be real at the input frequency and polarise at the reference voltage of the analogue digital converter, namely at a voltage $V_B$, for example equal to $V_{REF}/2$.

Figure 4B:
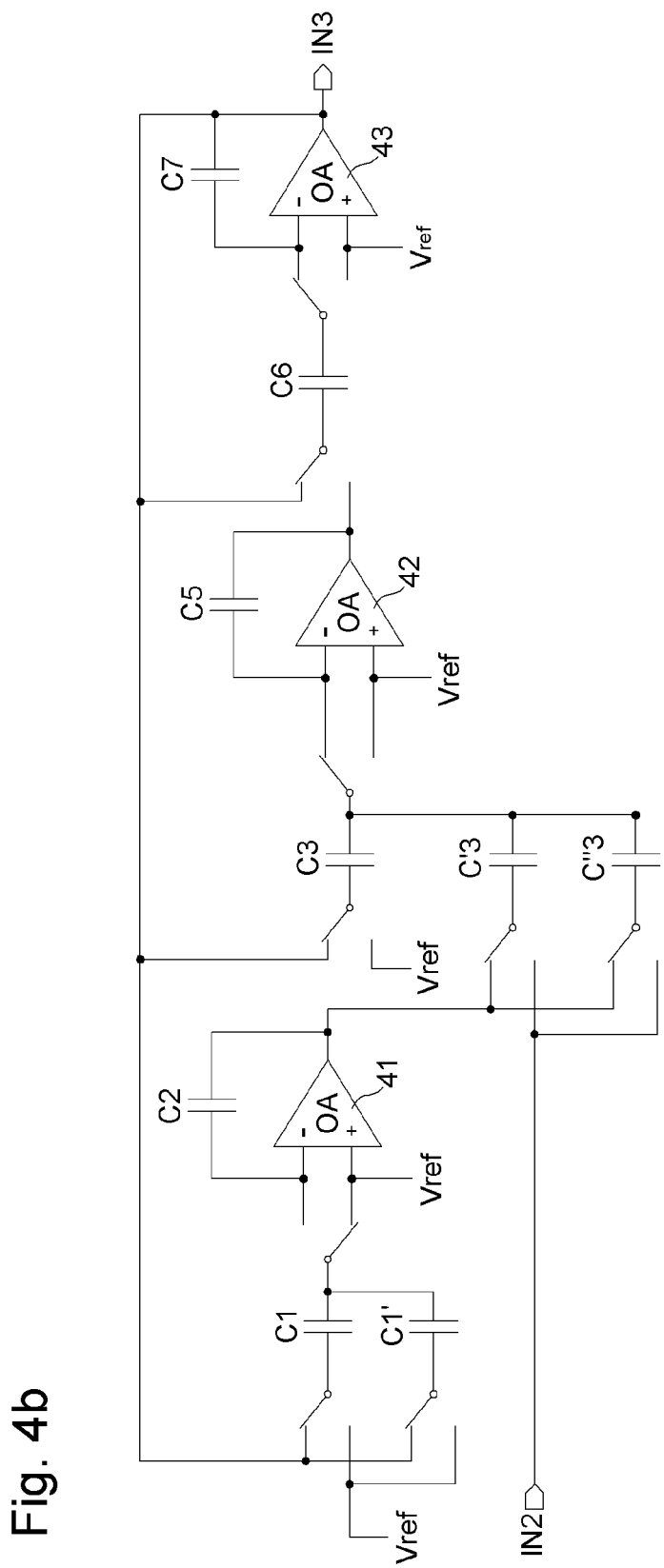
FIG. 4b shows the first section of a $5^{th}$ order bandpass filter of the third stage of the conditioning circuit.

FIG. 4b shows an example embodiment of the first section of the third stage comprising the $3^{rd}$ order bandpass filter. The embodiment of this bandpass filter is based on the switched capacitance technique. The filter requires the use of three operational amplifiers 41, 42 and 43 preceded by switchable capacitances. For one of the stages of this $3^{rd}$ order bandpass filter, it is advantageous to be able to program the gain by adjusting the capacitance ratio, for example by adding additional input capacitances C'1, respectively C"3, in parallel to the input capacitances (C1, respectively C'3).

Figure 4C:
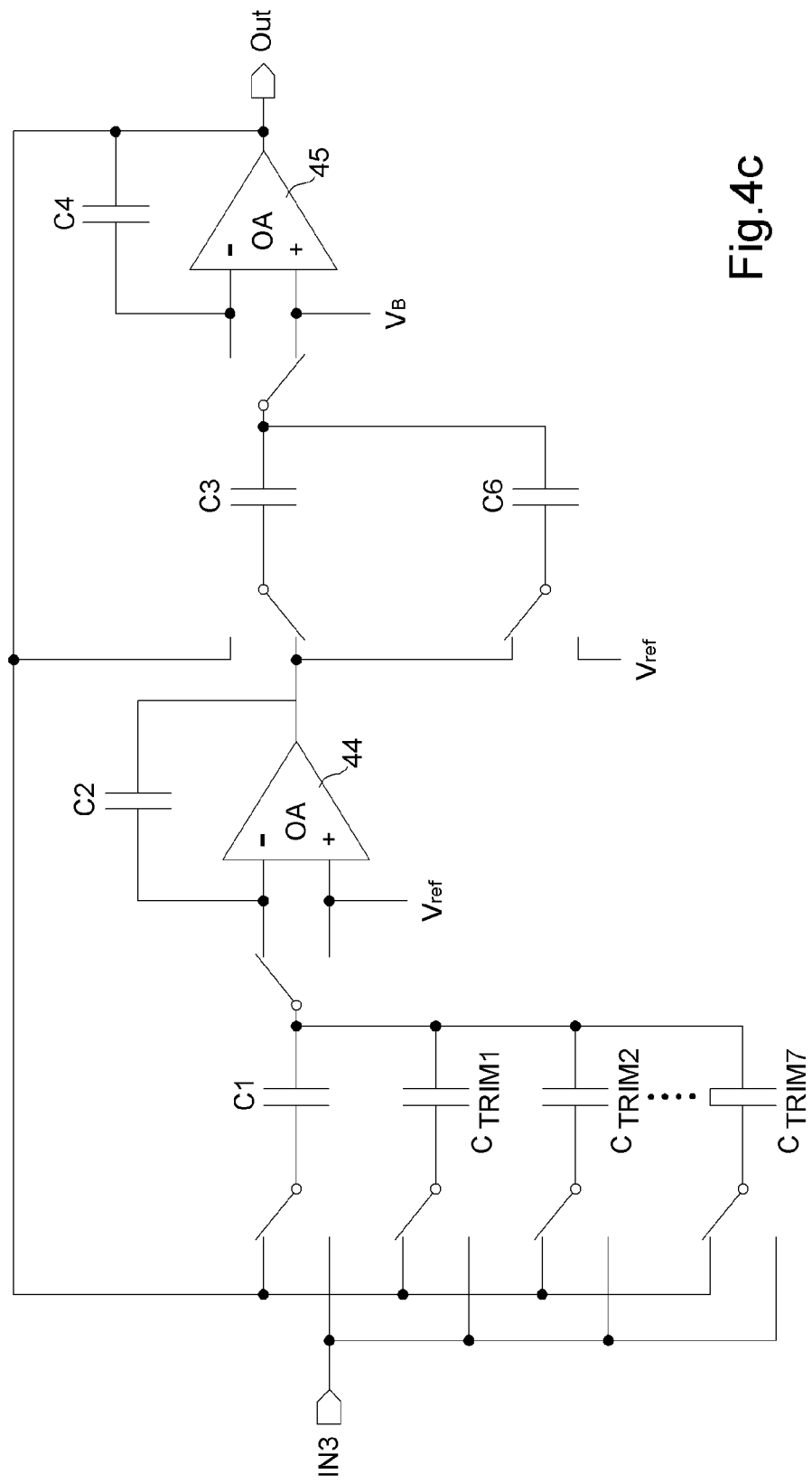
FIG. 4c shows the second section of a $5^{th}$ order bandpass filter of the third stage of the conditioning circuit.

FIG. 4c shows an example embodiment of the second section of the third stage comprising the $2^{nd}$ order low pass filter. The embodiment of this low pass filter is also based on the switched capacitance technique. The filter requires two operational amplifiers 44 and 45, the latter further being used for adapting impedance with the analogue digital converter of the processing unit placed at the output of the conditioning circuit. Here too, it is advantageous to provide an adjustable gain by playing on the capacitance ratio $C1/C_{TRIM1} \ldots /C_{TRIM7}$ placed at the input of the first stage of the filter comprising operational amplifier 44.

Figure 4D:
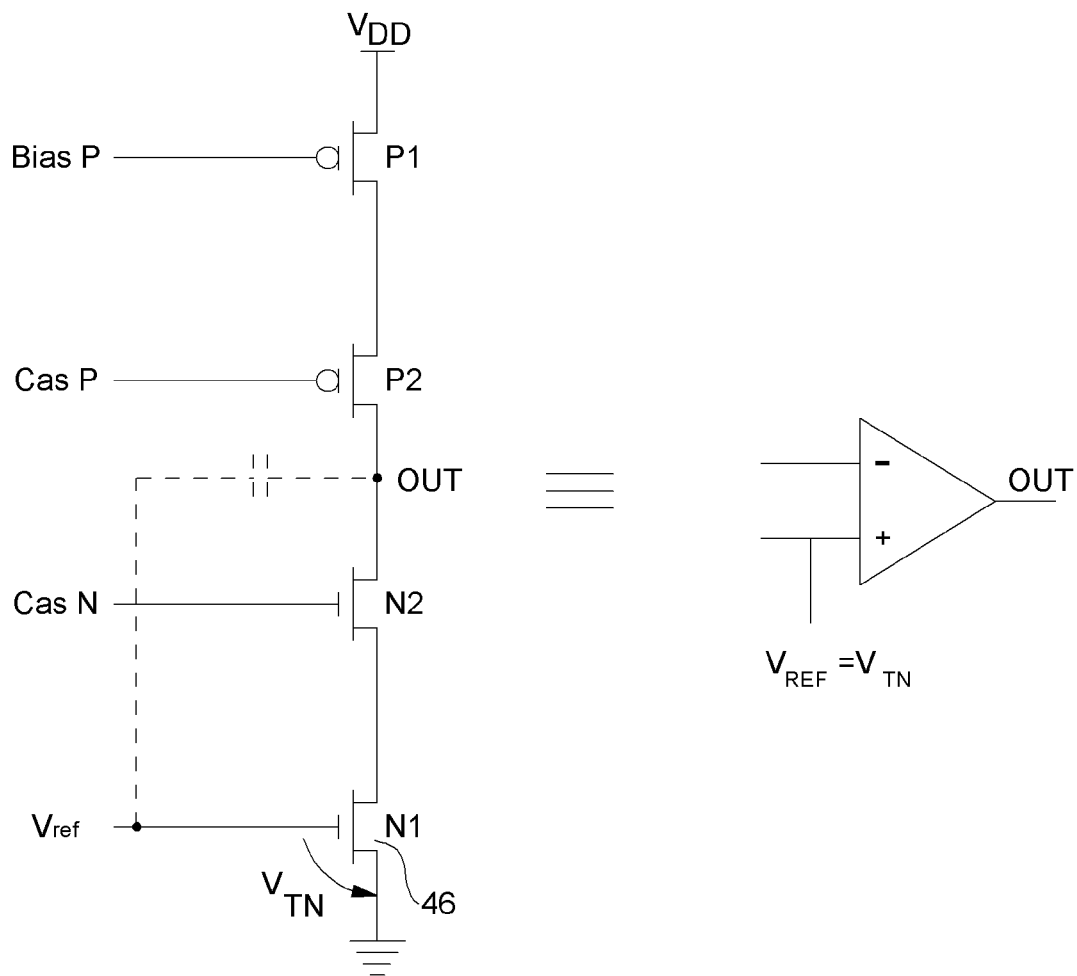
FIG. 4d shows a replacement circuit for each of the first four operational amplifiers of FIGS. 4b and 4c.
Figure 6:
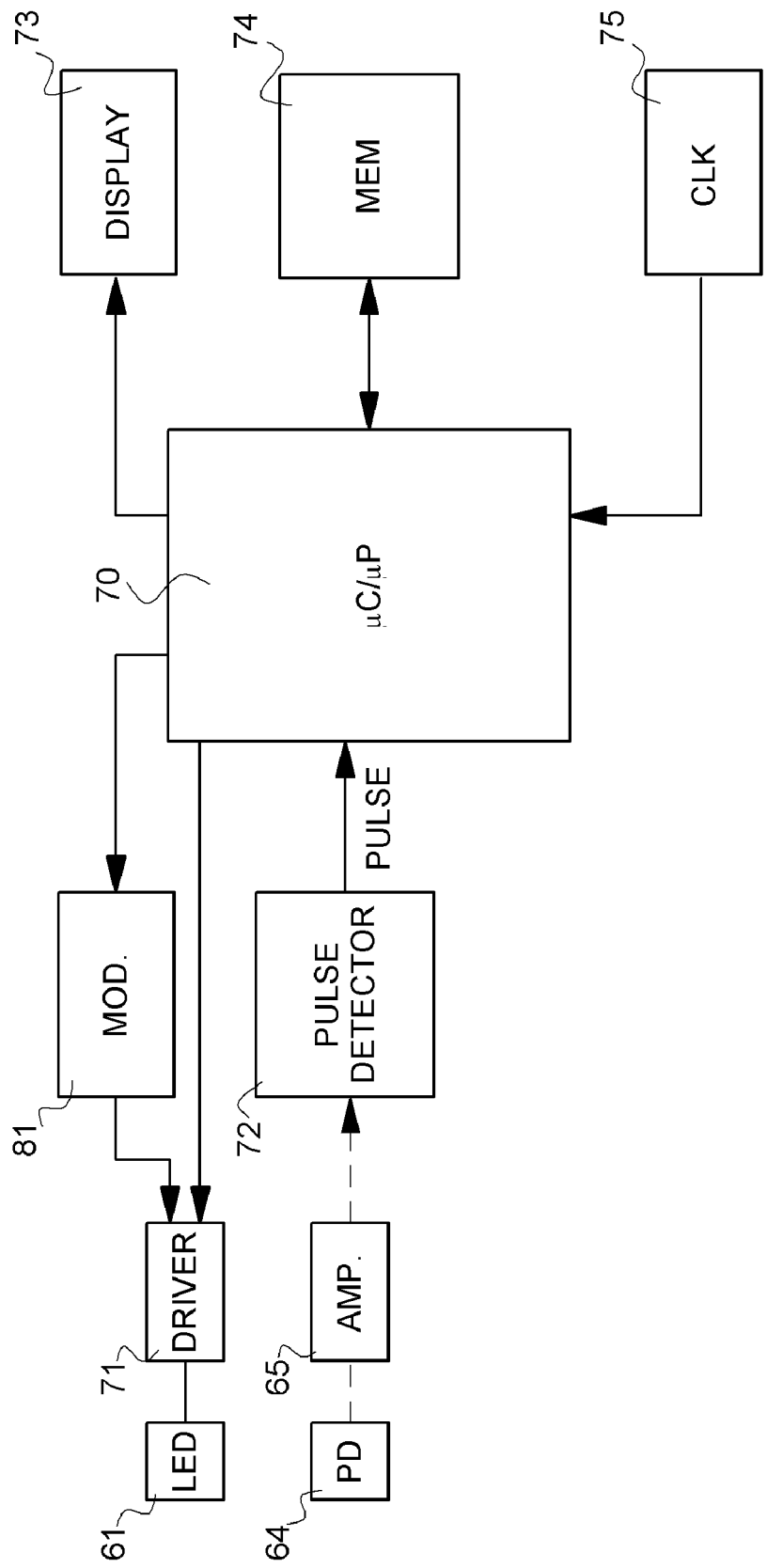
FIG. 6, already described, is a block diagram illustrating various components of a portable instrument according to the prior art.

According to a particularly advantageous embodiment of a $5^{th}$ order Bessel bandpass filter shown in relation to FIGS. 4b and 4c, the first four operational amplifiers 41, 42, 43 and 44 are replaced by four active transistors 46, this having the effect of drastically reducing the filter's current consumption and the overall circuit noise contribution. One of the replacement stages is shown in FIG. 4d, wherein the active transistor N1 46 replaces one operational amplifier. The reference voltage $V_{REF}$ is the threshold voltage $V_{TN}$ of the transistor. Transistors P1, P2 and N2 form the output of a current mirror whose input polarisation stage is common to all of the amplification stages of the filter and allow active transistor 46 to be polarised.

Figure 5:
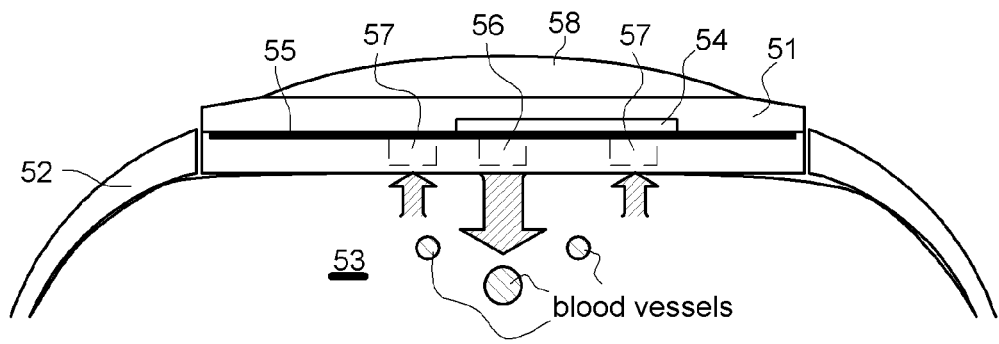
FIG. 5 is a cross-section of a portable electronic instrument comprising a conditioning circuit according to one embodiment of the invention.

FIG. 5 is a cross-section of a portable electronic instrument, such as for example a wristwatch, comprising a case 51, a wristband 52 for pressing watchcase 51 against the user's wrist 53. Case 51 contains an integrated circuit 54 mounted on a printed circuit board 55. Integrated circuit 54 includes a conditioning circuit according to one of the embodiments of the invention presented hereinabove. The portable instrument also includes an optical device 56, 57 which is permanently in contact with the organic tissue of the user when the instrument is being worn. A light emission is produced by a source 56 arranged to penetrate the organic tissue sufficiently deeply and to be modulated by the blood flow irrigating the illuminated organic tissue. The modulated light emission is detected after reflection by photoreceptors 57 of the optical device. The detected signals are then conditioned then treated respectively by the conditioning circuit and the processing unit integrated in integrated circuit 54. The portable instrument also includes a display device 58 for displaying information relating to the measurement of a physiological quantity, particularly the heart rate. It is of course also possible by way of alternative to use several integrated circuits, particularly a first integrated circuit for the light emission means and another integrated circuit for the reception means comprising the conditioning circuit and the processing unit, or any other desired variant.

Advantageously, integrated circuit 54 comprising the conditioning circuit also includes a programmable control circuit for the light source. This programmable control circuit is made in the form of a current source for powering light source 56. the current range can be adjusted by means of an external resistor. The purpose of this control circuit for light source 56 is to have a short set up time for generating short pulses.

It is important to have two reference voltages at the integrated circuit and more specifically the conditioning circuit, one used for powering the analogue digital converter of the processing unit and the other for polarising the last stage of the bandpass filter or the output stage of the third stage of the conditioning circuit. Advantageously, the polarisation voltage is selected as a fraction of the reference voltage necessary for powering the analogue digital converter. The polarisation voltage could for example correspond to half the reference voltage.

It will be understood that various alterations and/or improvements and/or combinations evident to those skilled in the art could be made to the various embodiments of the invention explained hereinabove without departing from the scope of the invention defined by the annexed claims.

What is claimed is:

1. A conditioning circuit for an external signal representative of a physiological quantity between an optical sensor and a processing unit, wherein the received external signal is broken down into a useful signal component and an ambient signal component, wherein said conditioning circuit includes:
   (a) a first stage including a transimpedance amplifier with an incorporated high pass filter using a feedback loop to subtract, at a stage input, the ambient signal component from the received external signal and to deliver, at a first output, an amplified useful signal;
   (b) a second stage including a blocker sampler circuit connected to demodulate said amplified useful signal and to deliver, at a second output, a demodulated useful signal; and
   (c) a third stage including a bandpass filter connected to filter said demodulated useful signal in a frequency band of the physiological quantity that is to be detected by the optical sensor, and the bandpass filter is connected to transmit a conditioned signal to said processing unit, wherein the bandpass filter is a $5^{th}$ order Bessel type filter comprising a switched capacitance circuit that includes a first $3^{rd}$ order bandpass filter in series with a $2^{nd}$ order low pass filter.

2. The conditioning circuit according to claim 1, wherein the blocker sampler circuit of the second stage includes correlated double sampling means for demodulating said amplified useful signal.

3. The conditioning circuit according to claim 2, wherein said correlated double sampling means are associated with a follower amplifier including a single active transistor.

4. The conditioning circuit according to claim 2, wherein each of N-1 first stages of the bandpass filter of said third stage uses a single active transistor.

5. The conditioning circuit according to claim 1, wherein each of N-1 first stages of the bandpass filter of said third stage uses a single active transistor.

6. The conditioning circuit according to claim 1, wherein gain of said bandpass filter is adjusted by altering at least one capacitance ratio.

7. An integrated circuit including a conditioning circuit for an external signal representative of a physiological quantity between an optical sensor and a first processing unit, wherein the received external signal is broken down into a useful signal component and an ambient signal component, wherein said conditioning circuit includes:
   (a) a first stage including a transimpedance amplifier with an incorporated high pass filter using a feedback loop to subtract, at a stage input, the ambient signal component from the received external signal and to deliver, at a first output, an amplified useful signal;
   (b) a second stage including a blocker sampler circuit connected to demodulate said amplified useful signal and to deliver, at a second output, a demodulated useful signal; and
   (c) a third stage including a bandpass filter connected to filter said demodulated useful signal in a frequency band of the physiological quantity that is to be detected by the optical sensor, and the bandpass filter is connected to transmit a conditioned signal to said first processing unit that is connected to receive said external signal transmitted by the optical sensor and to deliver the conditioned signal at a third output, wherein the bandpass filter is a $5^{th}$ order Bessel type filter comprising a switched capacitance circuit that includes a first $3^{rd}$ order bandpass filter in series with a $2^{nd}$ order low pass filter.

8. The integrated circuit according to claim 7, further including a second processing unit connected to the conditioning circuit, wherein the second processing unit receives said conditioned signal and processes said conditioned signal to supply information relating to said conditioned signal.

9. An electronic instrument worn on the wrist including the integrated circuit according to claim 7, wherein the electronic instrument further includes:
   an optical device for measuring a physiological quantity, wherein said optical device includes at least one light source for subjecting a portion of organic tissue to a light emission and at least one optical sensor for detecting intensity of the light emission after propagation in said organic tissue;
   wherein said integrated circuit is arranged for processing optical signals detected by said at least one optical sensor; and
   a display device for displaying information relating to measurement of the physiological quantity.

10. The electronic instrument according to claim 9, wherein the physiological quantity is heart rate.

11. An electronic instrument worn on the wrist including the integrated circuit according to claim 8, wherein the electronic instrument further includes:
   an optical device for measuring a physiological quantity, wherein said optical device includes at least one light source for subjecting a portion of organic tissue to a light emission and at least one optical sensor for detecting intensity of the light emission after propagation in said organic tissue;
   wherein said integrated circuit is arranged for processing optical signals detected by said at least one optical sensor; and
   a display device for displaying information relating to measurement of the physiological quantity measurement.

12. The electronic instrument according to claim 11, wherein the physiological quantity is heart rate.

13. The conditioning circuit according to claim 7, wherein a gain of said bandpass filter is adjusted by altering at least one capacitance ratio.

14. A conditioning circuit for an external signal representative of a physiological quantity between an optical sensor and a processing unit, wherein the received external signal is broken down into a useful signal component and an ambient signal component, wherein said conditioning circuit includes:
   (a) a first stage including a transimpedance amplifier with an incorporated high pass filter using a feedback loop to subtract, at a stage input, the ambient signal component from the received external signal and to deliver, at a first output, an amplified useful signal, wherein the transimpedance amplifier of the first stage comprises
      i. a voltage current converter; and
      ii. the feedback loop that includes a low pass filter and a current voltage converter;

(b) a second stage including a blocker sampler circuit connected to demodulate said amplified useful signal and to deliver, at a second output, a demodulated useful signal; and (c) a third stage including a bandpass filter connected to filter said demodulated useful signal in a frequency band of the physiological quantity that is to be detected by the optical sensor, and the bandpass filter is connected to transmit a conditioned signal to said processing unit, wherein the bandpass filter is a $5^{th}$ order Bessel type filter comprising a switched capacitance circuit including a first $3^{rd}$ order bandpass filter in series with a $2^{nd}$ order low pass filter.

15. The conditioning circuit according to claim 14, wherein the blocker sampler circuit of the second stage includes correlated double sampling means for demodulating said amplified useful signal.

16. The conditioning circuit according to claim 14, wherein a gain of said bandpass filter is adjusted by altering at least one capacitance ratio.

\* \* \* \* \*